(12) United States Patent
Aoshima et al.

(10) Patent No.: US 7,943,663 B2
(45) Date of Patent: May 17, 2011

(54) PROCESS AND AN APPARATUS FOR PRODUCING EPISESAMIN-RICH COMPOSITIONS

(75) Inventors: Yukihiro Aoshima, Osaka (JP); Masaaki Nakai, Osaka (JP); Kenji Katano, Osaka (JP); Asako Okada, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 468 days.

(21) Appl. No.: 11/992,196

(22) PCT Filed: Sep. 29, 2006

(86) PCT No.: PCT/JP2006/319493
§ 371 (c)(1),
(2), (4) Date: Mar. 18, 2008

(87) PCT Pub. No.: WO2007/037385
PCT Pub. Date: Apr. 5, 2007

(65) Prior Publication Data
US 2009/0163583 A1    Jun. 25, 2009

(30) Foreign Application Priority Data

Sep. 30, 2005  (JP) ................................. 2005-288660
Sep. 30, 2005  (JP) ................................. 2005-288827
Oct. 7, 2005   (JP) ................................. 2005-295059

(51) Int. Cl.
*A61K 31/36* (2006.01)
(52) U.S. Cl. ...................................... 514/465; 514/464
(58) Field of Classification Search .................. 514/464, 514/465; 422/187
See application file for complete search history.

(56) References Cited

U.S. PATENT DOCUMENTS

| 5,211,953 A | 5/1993 | Shinmen et al. |
| 2005/0095233 A1 | 5/2005 | McCleary et al. |
| 2006/0058376 A1 | 3/2006 | Moritani |
| 2007/0208077 A1 | 9/2007 | Ono |
| 2008/0275110 A1 | 11/2008 | Ono et al. |
| 2009/0156838 A1 | 6/2009 | Aoshima |
| 2009/0163583 A1 | 6/2009 | Aoshima |
| 2009/0202643 A1 | 8/2009 | Yamada |

FOREIGN PATENT DOCUMENTS

CN          1796388 A          7/2006
(Continued)

OTHER PUBLICATIONS

Biswanath Das et al., "Clay Catalysed Convenient Isomerization of Natural Furofuran Lignans Under Microwave Irradiation", Synthetic Communications, 2000, pp. 4001-4006, vol. 30, No. 22, Published by Marcel Dekker, Inc.

(Continued)

*Primary Examiner* — Taylor Victor Oh
(74) *Attorney, Agent, or Firm* — Drinker Biddle & Reath LLP

(57) ABSTRACT

To provide a process and an apparatus by means of which a composition that contains episesamin in a concentration greater than 50 wt % on the basis of the sum weight of sesamin and episesamin can be produced conveniently and at high yield.
There are provided a process and an apparatus which comprise the step of applying epimerization to sesamin or a sesamin-containing composition so that at least part of the sesamin is converted to episesamin and the step of selectively crystallizing episesamin by recrystallization and by means of which a composition that contains episesamin in a concentration greater than 50 wt % can be produced conveniently and at high yield.

13 Claims, 1 Drawing Sheet

FOREIGN PATENT DOCUMENTS

| | | |
|---|---|---|
| EP | 387000 | 9/1990 |
| EP | 0 409 654 | 1/1991 |
| EP | 0 488 513 | 6/1992 |
| EP | 0 729 753 | 9/1996 |
| EP | 0 782 827 A1 | 7/1997 |
| EP | 1 930 333 A1 | 6/2008 |
| EP | 1 950 214 A1 | 7/2008 |
| GB | 1 432 784 | 4/1976 |
| JP | 49-71127 A | 7/1974 |
| JP | 54-92616 A | 7/1979 |
| JP | 59-013717 A | 1/1984 |
| JP | 3-27319 | 2/1991 |
| JP | 3-53866 | 3/1991 |
| JP | 4-9331 | 1/1992 |
| JP | 4-159221 | 6/1992 |
| JP | 5-51388 | 3/1993 |
| JP | 6-227977 | 8/1994 |
| JP | 8-268887 | 10/1996 |
| JP | 10-120695 | 5/1998 |
| JP | 11-269456 | 10/1999 |
| JP | 2001-139579 | 5/2001 |
| JP | 4-261120 | 9/2002 |
| JP | 2006-280276 A | 10/2006 |
| JP | 2006-306864 | 11/2006 |
| WO | WO 97/01968 | 1/1997 |
| WO | WO 2004/064830 A1 | 8/2004 |
| WO | WO 2004/105749 A1 | 12/2004 |
| WO | WO 2005/095414 A1 | 10/2005 |
| WO | WO 2006/016682 A1 | 2/2006 |
| WO | WO 2006/070856 | 7/2006 |
| WO | WO 2006/106926 A1 | 10/2006 |

OTHER PUBLICATIONS

Y. Fukuda et al., "Contribution of Lignan Analogues to Antioxidative Activity of Refined Unroasted Sesame Seed Oil", J. Am. Oil Chem. Soc., Aug. 1986, pp. 1027-1031, vol. 63, No. 8.

International Search Report dated Nov. 28, 2006 for PCT/JP2006/319493 filed Sep. 29, 2006.

Namiki et al., "Goma—Sono Kagaku to Kinousei", Maruzen Planet Co., Ltd. (1998) p. 47, lines 3-4, and p. 51, lines 12-16 (partial translation).

Shimizu, Sakayu et al., "Production of Dihomo-γ-linolenic Acid by *Mortierella alpina* 1S-4", JAOCS, vol. 66, No. 2 (Feb. 1989) pp. 237-241.

Shimizu, Sakayu et al., "Sesamin is a Potent and Specific Inhibitor of Δ5 Desaturase in Polyunsaturated Fatty Acid Biosynthesis", Lipids, vol. 26, No. 7 (1991), pp. 512-516.

Umeda-Sawada, Rumi et al., The Metabolism and Distribution of Sesame Lignans (sesamin and episesamin) in Rats, Lipids, vol. 34, No. 6 (1999), pp. 633-637.

Kushiro, Masayo et al., "Comparative Effect of Sesamin and Episesamin on the Activity and Gene Expression of Enzymes in Fatty Acid Oxidation and Synthesis in Rat Liver", Journal of Nutritional Biochemistry 13 (2002) pp. 289-295.

Supplementary European Search Report mailed Nov. 4, 2010, in European Application No. EP 06 79 8461.

International Preliminary Report on Patentability dated Oct. 21, 2008 in PCT/JP2007/055113.

Extended European Search Report dated Sep. 14, 2009 issued in European Application No. 07 738 583.9.

Final Office Action mailed Aug. 25, 2010, in U.S. Appl. No. 12/295,078.

Office Action mailed Jan. 7, 2010, in U.S. Appl. No. 12/295,078.

PROCESS AND AN APPARATUS FOR PRODUCING EPISESAMIN-RICH COMPOSITIONS

CROSS REFERENCE TO RELATED APPLICATIONS

This application is the National Stage of International Application No. PCT/JP2006/319493, filed Sep. 29, 2006, and claims benefit of Japanese Application Nos. 2005-288660 and 2005-288827, filed Sep. 30, 2005, and Japanese Application No. 2005-295059 filed Oct. 7, 2005, all of which are herein incorporated by reference in their entirety.

TECHNICAL FIELD

This invention relates to a process and an apparatus for producing episesamin-rich compositions that contain episesamin in concentrations greater than 50 wt %; more specifically, this invention relates to a process and an apparatus for producing episesamin-rich compositions that contain episesamin in amounts greater than 50 wt %, preferably 60 wt % and upward, more preferably 70 wt % and upward, by subjecting sesamin or a sesamin-containing composition to epimerization so that the sesamin is epimerized to yield an episesamin-enriched, sesamin- and episesamin-containing mixture, and then recrystallizing the epimerized mixture of episesamin and sesamin.

BACKGROUND ART

Episesamin is a stereoisomer of sesamin. To be more specific, sesamin is an optically active compound having the structure represented by formula I:

[Formula 1]

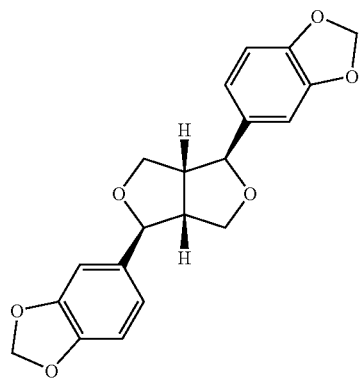

I and episesamin, an isomer of sesamin, is an optically active compound having the structure represented by formula II:

[Formula 2]

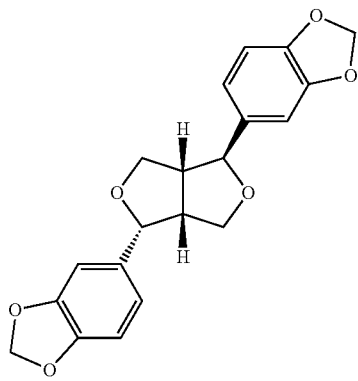

II

As is clear from the two formulas, sesamin has a symmetrical structure in the plane whereas episesamin has an asymmetric structure.

Sesamin is one of the principal lignan compounds in sesame and is contained in sesame seeds in amounts of 0.1-0.5%. In contrast, episesamin does not naturally occur in sesame seeds but when sesame oil obtained by pressing is passed through the step of refining to salad oil of higher purity and the like, sesamin undergoes epimerization to give episesamin as a by-product (non-patent reference 1), and sesamins refined from the refined sesame oil are known to contain sesamin and episesamin in proportions of nearly 1:1 by weight ratio (non-patent reference 2).

Experiments with mixtures of sesamin and episesamin (at ca. 1:1) have revealed various physiological activities of sesamins including, for example, the action of inhibiting Δ5-unsauration enzymes (non-patent references 3 and 4, as well as patent reference 1), anti-oxidizing action against lipids (patent references 2 and 3), antihypertensive action (patent reference 4), the action of improving hepatic functions (patent reference 5), the action of scavenging active oxygen (patent reference 6), the blood cholesterol lowering action and/or cholesterol lowering action (patent references 7 and 8), the action of in vivo stabilization of highly unsaturated fatty acids (patent reference 9), and the action of preventing sickness from drinking (patent reference 10).

Recent studies have also revealed the differences between the physiological activities of sesamin and episesamin. For example, rats administered orally with a mixture of sesamin and episesamin (ca. 1:1) were shown to have such an in vivo distribution that the transfer of episesamin into organs was at least twice as much as that of sesamin (non-patent reference 5). In addition, experiments where rats were separately administered orally with sesamin and episesamin yielded a report showing that episesamin markedly increased the gene expression and enzymatic activity of β-oxidation enzymes in the liver as compared with sesamin and that there was no difference between sesamin and episesamin in terms of activity for inhibiting fatty acid synthases (non-patent reference 6). These are a few of the reports that have recently been made of the beneficiary effects of episesamin.

Methods so far proposed for sesame lignan production include extracting sesame oil with organic solvents such as alcohol (e.g. methanol), acetone, petroleum ether and acetonitrile, or mixtures of these solvents with water, as well as subjecting sesame oil to molecular distillation (patent reference 11).

[Patent reference 1] the official gazette of JP 3-27319 A
[Patent reference 2] the official gazette of JP 5-051388 A
[Patent reference 3] the official gazette of JP 2001-139579 A
[Patent reference 4] the official gazette of JP 8-268887 A
[Patent reference 5] the official gazette of JP 4-099331 A
[Patent reference 6] the official gazette of JP 6-227977 A
[Patent reference 7] the official gazette of Japanese Patent No. 3001589
[Patent reference 8] the official gazette of JP 4-159221 A
[Patent reference 9] the official gazette of JP 11-269456 A
[Patent reference 10] the official gazette of Japanese Patent No. 3124062
[Patent reference 11] the official gazette of JP 10-120695 A
[Non-patent reference 1] Namiki et al., "Goma—Sono Kagaku to Kinousei (Sesame—Its Science and Functions)", Maruzen Planet Co., Ltd. (1998)
[Non-patent reference 2] Fukuda, Y. et al., J. Am. Oil Chem. Soc., 63, 1027-1031 (1986)
[Non-patent reference 3] S. Shimizu et al., J. Am. Oil Chem. Soc., 66, 237-241 (1989)
[Non-patent reference 4] S. Shimizu et al., Lipid, 26, 512 (1991)
[Non-patent reference 5] Sawada, R. et al., Lipids, 34, 633 (1999)
[Non-patent reference 6] Kushiro, M. et al., J. Nutr. Biochem., 13, 289-295 (2002)

DISCLOSURE OF THE INVENTION

Problems to be Solved by the Invention

As described above, episesamin has been reported to have beneficiary effects. Among methods so far known to be available for obtaining episesamin-rich compositions that contain episesamin in concentrations greater than 50 wt % is the process of isolation from an episesamin-containing mixture by, for example, column chromatography. However, those methods involve complicated operations and, what is more, they can yield so small quantities of the composition at a time that they feature only low efficiency. Therefore, it is desired to establish a production process and apparatus that are more convenient and feature higher yield.

An object of the present invention is to provide a process and an apparatus that convert sesamin into episesamin through epimerization and then recrystallize the sesamin- and episesamin-containing mixture, whereby a composition that contains episesamin in a proportion greater than 50 wt %, preferably 60 wt % and upward, more preferably 70 wt % and upward, on the basis of the sum weight of the sesamin and episesamin can be produced conveniently and at high yield.

Means for Solving the Problems

As a result of intensive studies made in order to attain the above-stated object, the present inventors found that sesamin and episesamin had different solubilities in certain specified oils or fats. Making use of this difference in solubility, the present inventors tested the recrystallization technique in the specified oils or fats and found that episesamin could be separated from a mixture of sesamin and episesamin having similar structures. Thus, the present inventors established a method comprising the steps of dissolving under heating a mixture containing sesamin and episesamin (which is hereinafter designated a sesamin/episesamin mixture) in an oil or fat and then recrystallizing the solution such that episesamin will crystallize selectively, whereby a composition containing episesamin in a proportion greater than 50 wt %, preferably 60 wt % and upward, more preferably 70 wt % and upward, can be produced conveniently and at high yield. This has led to the accomplishment of the present invention.

The present inventors also found that the technique of epimerizing sesamin by acidic catalyst treatment with could be utilized for industrial production of episesamin-rich compositions. Accordingly, epimerization by this acidic catalyst treatment was combined with the technique of recrystallization in the specified oil or fat, enabling the present inventors to accomplish the present invention which produces a sesamin/episesamin mixture containing an increased proportion of episesamin.

In short, the present inventors adopted the following approach (1) or (2) to establish a method by which compositions containing episesamin in concentrations greater than 50 wt %, preferably 60 wt % and upward, more preferably 70 wt % and upward, could be produced conveniently and at high yield, as well as an apparatus to be used in the method. This has led to the accomplishment of the present invention.

(1) The step of acidic catalyst treating sesamin or a sesamin-containing composition (including a sesamin/episesamin mixture) to epimerize the sesamin and the step of causing episesamin to selectively crystallize from the resulting mixture containing both sesamin and episesamin (which is hereinafter designated a sesamin/episesamin mixture) by means of recrystallization are combined so as to produce a composition that contains episesamin at high concentration.

(2) A sesamin/episesamin mixture is used as a feed, which is not subjected to the acidic catalyst treatment but simply subjected to recrystallization in an oil or fat so as to produce a sesamin/episesamin mixture containing episesamin at a concentration greater than 50 wt %. The sesamin/episesamin mixture which is to be used as a feed in this method may be one that is obtained by epimerizing sesamin through acidic catalyst treatment; applicable sesamin/episesamin mixtures also include ones that are obtained by other methods such as specified refining and extracting methods.

In addition, the present inventors developed an apparatus comprising an isomerizing unit that epimerizes sesamin either on its own or as the sesamin content of a sesamin-containing composition by acidic catalyst treatment, a crystallizing unit that recrystallizes the sesamin/episesamin mixture using an oil or fat, and a fluid channel communicating the isomerizing unit with the crystallizing unit; more specifically, the present inventors developed an apparatus comprising a reactor (mixing vessel) for mixing a sesamin-containing oil or fat with an acidic catalyst to effect an isomerization reaction, a crystallizer (crystallizing vessel) for performing recrystallization, and a fluid feed pipe (fluid channel) for feeding the reaction solution from the reactor into the crystallizing vessel, the fluid feed pipe optionally having a filtering means. The present inventors confirmed that using those apparatuses, a sesamin/episesamin mixture containing episesamin at high concentration could be obtained from the sesamin-containing oil or fat conveniently and at high yield and this has led to the completion of the apparatus of the present invention.

Advantage of the Invention

By means of the present invention, compositions containing episesamin at concentrations greater than 50 wt % can be industrially produced from sesamin or sesamin-containing compositions conveniently and in high yield.

KEY TO SYMBOLS

Figure 1:
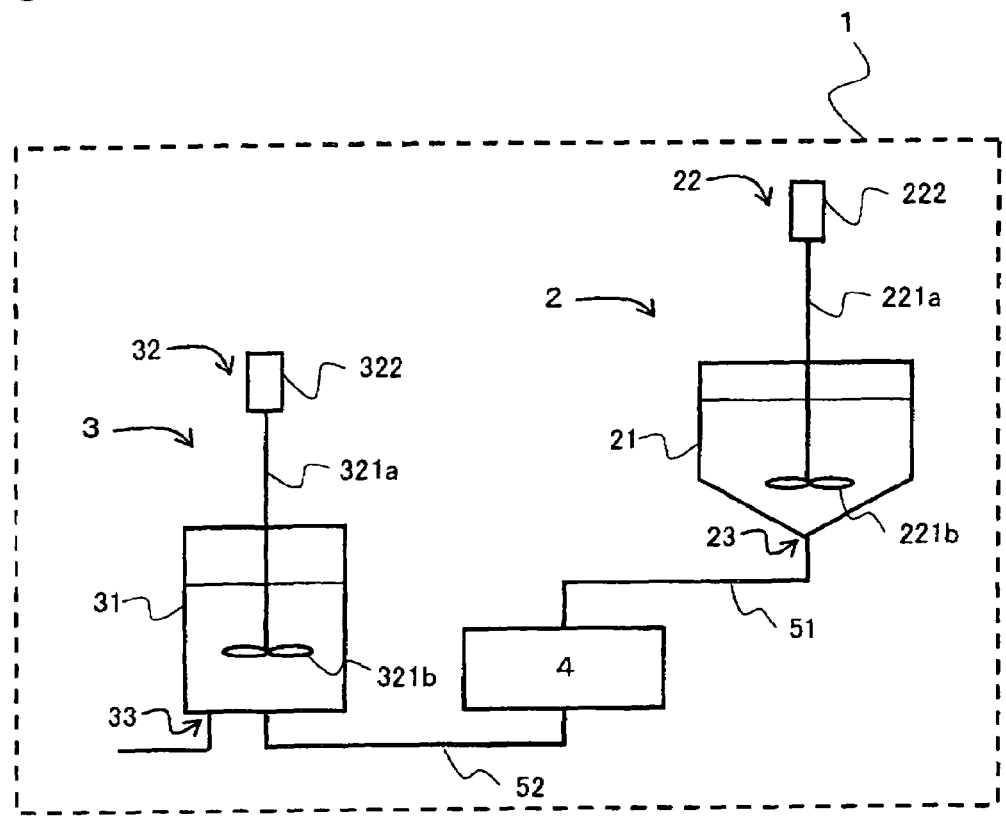
[FIG. 1] A schematic view showing an embodiment of the apparatus of the present invention for producing compositions that contain episesamin at high concentration.

1: production apparatus; 2: isomerizing unit; 3: recrystallizing unit; 4: filtering means; 51, 52: fluid channel

BEST MODES FOR CARRYING OUT THE INVENTION (Epimerization)

The production process of the present invention starts with epimerizing sesamin or a sesamin-containing composition so that at least part of the sesamin is epimerized, thereby preparing a mixture containing both sesamin and episesamin. Sesamin or the sesamin-containing composition that serve as the feed can be isolated from within sesame seeds or refined from sesame oil by known methods. Typically, the following procedure can be taken.

First, an extract the main component of which is the sesamin-containing composition to be used in the present invention is obtained from sesame oil. To this end, extracting and concentrating steps are performed using various organic solvents that are substantially immiscible with sesame oil and which can extract and dissolve the sesamin-containing composition. Examples of such organic solvents include acetone, methyl ethyl ketone, diethyl ketone, methanol, ethanol, etc.

Alternatively, an extract the main component of which is sesamin to be used in the present invention may be obtained from sesame oil. To this end, sesame oil is mixed uniformly with any of the solvents mentioned above and the mixture is thereafter left to stand at low temperature; the mixture is then subjected to phase separation by the usual method such as centrifugation and the solvent is evaporated away from the solvent fraction. More specifically, sesame oil is dissolved in 2-10 volumes, preferably 6-8 volumes, of acetone, and the solution is left to stand overnight at a suitable temperature that depends on the type of the organic solvent used; the temperature may be subfreezing, typically at −10° C. or below, preferably at −20° C. or below, say, at ca. −80° C. As a result, the oil component forms a precipitate and the organic solvent is distilled off the filtrate obtained by filtration, whereupon an extract is obtained that contains sesamin as a main component.

Alternatively, sesame oil is mixed with hot methanol or hot ethanol; the mixture is then left to stand at room temperature and the solvent is evaporated away from the solvent fraction. Specifically, sesame oil is mixed with 2-10 volumes, preferably 5-7 volumes, of hot methanol (at 50° C. and above) or hot ethanol (at 50° C. and above) and extraction is performed under vigorous agitation. Subsequently, the mixture is either left to stand at room temperature or subjected to phase separation by the usual method such as centrifugation and the solvent is distilled off the solvent fraction, whereupon an extract is obtained that contains sesamin as a main component. If desired, supercritical gas extraction may be employed.

From these extracts, the sesamin-containing composition as the feed to be used in the present invention may be obtained by treating them in accordance with the usual method such as column chromatography, high-performance liquid chromatography, recrystallization, distillation, liquid-liquid countercurrent partition chromatography, etc., so that the desired mixture is isolated.

These isolation methods are described more specifically. The extracts mentioned above are recovered by high-performance liquid chromatography on a reverse-phase column (ODS) using methanol/water (60:40) as an eluant; after distilling off the solvent, the resulting crystal is subjected to recrystallization from ethanol, producing sesamin or a sesamin-containing composition that can be used in the present invention.

The sesame oil to be used in the present invention may be a refined product or it may be a crude product obtained at any of the stages of sesame oil production prior to decoloration. If desired, sesame oil may be replaced by sesame seeds or sesame cake (sesame seeds from which oil has been expressed to a residual oil content of 8-10%). In this case, the sesame seeds or sesame cake may be crushed depending on the need, followed by extracting in the usual manner using any solvent, for example, one of the solvents mentioned above in connection with extraction from sesame oil. After separating the extraction residue, the solvent is removed from the liquid extract by evaporation or the like, yielding the extract.

From the thus prepared sesame seed extract, sesame cake extract or crude form of sesame oil, one can obtain sesamin or the sesamin-containing composition by a similar technique. Note that sesamin obtained from Asiasari Radix is comparable in effectiveness to the sesamin obtained from sesame seeds, sesame cake and sesame oil, and these optically active forms can also be employed in the present invention. In addition, mixtures that can be used as the feed in the present invention are obtained from by-products to the process of sesame oil production.

Note that the method of refining the sesamin and sesamin-containing composition that are to be used in the present invention and the method of yielding the extract are by no means limited to those described above. In addition, the sesamin-containing composition to be used in the present invention is by no means limited to those obtained from sesame oil, sesame cake, and sesame seeds, and all natural products that contain the above-mentioned sesamin compounds of the present invention may be employed. Examples of such natural products include Acanthopoanacis Cortex, *paulownia* tree, *ginkgo* bark, *Piper retrofractum,* Asiasari Radix, etc.

In the process of the present invention for producing episesamin-rich compositions, the sesamin or sesamin-containing composition obtained in the manner described above is subjected to epimerization treatment so that at least part of the sesamin is epimerized to prepare a mixture containing both sesamin and episesamin. The present inventors studied the mechanism of epimerization and found that by protonating sesamin having the structure shown by formula I:

[Formula 3]

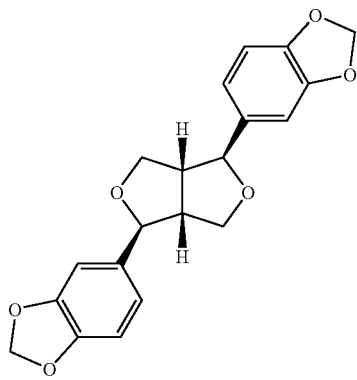

so as to cause a ring-opening reaction, the isomer episesamin was generated. Therefore, the epimerization that occurs in the production process of the present invention is not limited in any particular way as long as it can cause a ring-opening reaction to occur in sesamin, thus generating episesamin, and it may be exemplified by acidic catalyst treatment, heat treatment in the presence of a mineral acid, and the like. Among these methods, the acidic catalyst treatment is preferred from the viewpoints of efficiency in epimerization (ease of conversion to episesamin) and operability.

Acid catalysts to be used in the acid catalyst treatment include inorganic or organic Brønsted acids such as sulfuric acid, hydrochloric acid, phosphoric acid and boric acid, Lewis acids such as aluminum chloride, iron chloride, tin chloride and titanium chloride, montmorillonite catalysts such as acid clay and activated clay, and solid catalysts typified by zeolite and silica alumina catalysts, and these can be used either alone or in combination of two or more kinds. Considering the reaction efficiency, post-treatment and other factors, the use of activated clay is preferred. In this connection, the present inventors had found that when a 5% aqueous suspension of acid clay having a pH of 5 or more was rendered to have a lower pH by adding a strong acid such as hydrochloric acid to the reaction solution during reaction (the pH preferred by the 5% aqueous suspension is 3.7 or less), the epimerization efficiency was as high as what is obtained by using activated clay. Therefore, acid clay that is adjusted to have a lower pH by addition of an acid can also be used with advantage.

Note here that if refined sesame oil is used to prepare the above-described sesamin or sesamin-containing composition, the epimerization that is occasionally effected during the purification process will eventually enable one to obtain a sesamin/episesamin mixture. In this case, the epimerization step of the present invention may be omitted; however, the present inventors have found that even when the sesamin/episesamin mixture is used as the starting feed, the concentration of episesamin in the crystal can be increased by applying the acidic catalyst treatment (activated clay treatment). The reason for the better result that can be obtained by applying the acidic catalyst treatment is not known but it is preferred to apply the acidic catalyst treatment even when the sesamin/episesamin mixture is used.

Thus, the starting feed to be subjected to epimerization in accordance with the present invention may be sesamin as one of those that have already been refined to a purity of almost 100% or it may be the sesamin/episesamin mixture. In the case of the sesamin/episesamin mixture, one may use a mixture in which the weight ratio of sesamin to episesamin is generally between 99.9:0.1 and 40:60.

Sesamin and/or episesamin can also be obtained by synthesis. For example, it is known that they can be synthesized by the method of Beroza et al. [J. Am. Chem. Soc. 78, 1242 (1956)], the method of Takano et al. [J. Chem. Soc. Chem. Commun. p. 189 (1988)] or the method of Suginome et al. [J. Org. Chem. 60, p. 3052 (1955)]. Here again, the above-described step of epimerization may be omitted if the sesamin/episesamin mixture is obtained.

(Oil or Fat)

According to the production process of the present invention, sesamin or the sesamin-containing composition (including the sesamin/episesamin mixture) is dissolved, either before or after epimerization, in an oil or fat under heating to form a solution and the recrystallization step is applied in the solution, whereby one can obtain a composition containing episesamin in high concentration. Therefore, the oil or fat that dissolves sesamin or the sesamin-containing composition (including the sesamin/episesamin mixture) in the present invention is preferably one that differs in its ability to dissolve sesamin and episesamin because they can be separated easily enough during recrystallization. Specific examples of the oil or fat that can be used include MCT (middle-chain fatty acid triglyceride), diacyl glycerol, sesame salad oil, olive oil, soybean oil, rapeseed oil, corn oil, rice germ oil, and sunflower seed oil. In particular, MCT (middle-chain fatty acid triglyceride) is preferably used. Shown below are the solubilities of sesamin and episesamin in MCT.

| [Expression 1] | |
|---|---|
| Solubility in MCT | (w/w %) |
| Sesamin | 4.0 |
| Episesamin | 2.5 |

For the sake of convenience, the oils or fats that can be used in the present invention include free fatty acids such as octanoic acid and fatty acid esters such as octyl acetate.

The present invention is characterized by recrystallizing the sesamin-containing composition in an oil or fat. If the feed is sesamin or a sesamin/episesamin mixture of low episesamin content, it is preferred to epimerize the sesamin prior to recrystallization and then recrystallize the epimerized episesamin. Use of recrystallization in oils or fats has not been known to date but the viscosity of oils or fats is not considered to affect recrystallization (crystallization) (see Example 3) and, hence, as noted above, the oil or fat to be used in the present invention is preferably selected from among oils and fats that differ in their ability to dissolve sesamin and episesamin and they are not particularly limited in such aspects as viscosity.

Sesamin or the sesamin-containing composition (including the sesamin/episesamin mixture) is dissolved in the above-mentioned oils or fats and the method of dissolving them is not limited in any particular way. Depending on the concentration of sesamin or the sesamin-containing composition (including the sesamin/episesamin mixture) and on the kind of the oil or fat used, they are dissolved by heating generally at 60° C.-160° C., preferably at 80° C.-140° C. and holding that temperature for 5-30 minutes.

In the production process of the present invention, sesamin or the sesamin-containing composition (including the sesamin/episesamin mixture) is dissolved under heating and, thereafter, depending on the need, the solution is subjected to the acidic catalyst treatment (epimerization) and the resulting epimerized product is recrystallized to separate a composition that contains episesamin in a concentration greater than 50 wt %. Although recrystallization is effected in the oil or fat, the concentration of the solute (episesamin) in the oil or fat during recrystallization, the presence or absence of seed crystals, the cooling rate, etc. are not limited in any particular way and may be determined in the same manner as in ordinary recrystallization which uses water or organic solvents. Specifically, an oil solution that is obtained by the acidic catalyst treatment and which contains the sesamin/episesamin mixture (ca. 1:1) in a concentration of about 2%-50% is put into a crystallizer and slowly cooled, either with agitation or by standing, in the presence of about 0.1%-20% of seed crystals at a temperature that maintains a supersaturated state, desirably in a range of 5° C.-90° C., whereby a crystal slurry is produced that contains episesamin at a concentration greater than 50 wt %. From the thus obtained slurry, one can recover the desired episesamin-rich composition as crystal by the steps of filtration in the presence of an added ethyl alcohol or the like, solvent removal, and drying.

The filtrate resulting from the recovery process has a residue of sesamin that has not been recrystallized (sesamin in the feed or yet to be epimerized sesamin), so depending on the need, a fresh supply of sesamin may be added to this filtrate and the resulting product of an increased sesamin concentration may be recycled as the starting feed in the production process of the present invention. Sesamin is expensive and from an economic viewpoint, it is preferred to produce fresh episesamin by recycling sesamin.

The present invention provides a process for producing episesamin-rich compositions that comprises the steps of dissolving sesamin or a sesamin-containing composition in an oil or fat with heat, optionally applying an acidic catalyst treatment to the resulting oil or fat solution, and selectively crystallizing the epimerization-obtained episesamin by recrystallization.

(Production Apparatus)

On the following pages, a mode of implementing the apparatus of the present invention for producing a composition containing episesamin at high concentration is described in detail with reference to the accompanying drawings.

Figure 2:
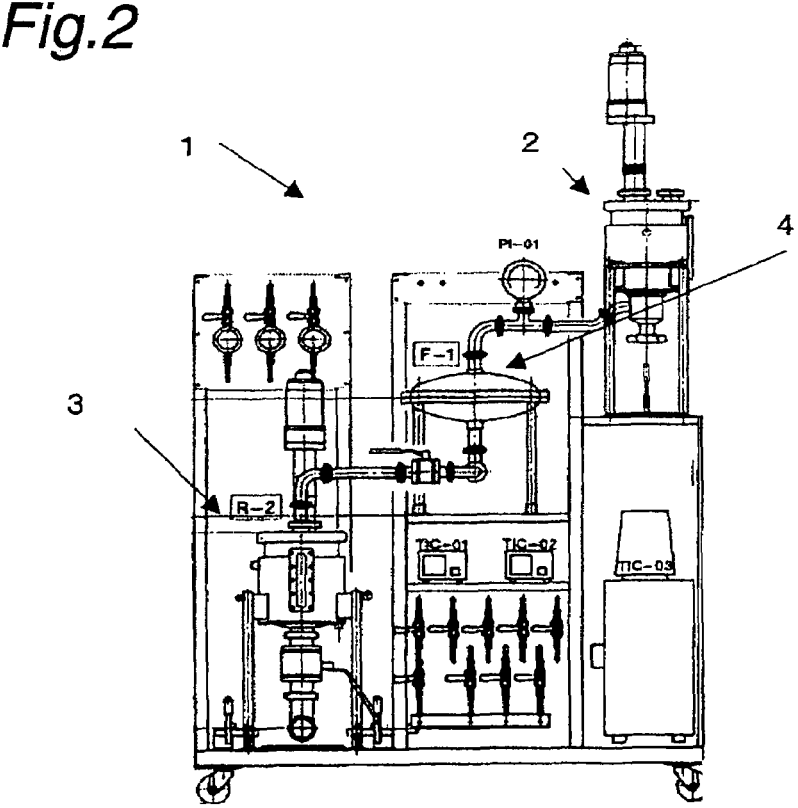
[FIG. 2] An exterior view showing an embodiment of the apparatus of the present invention for producing compositions that contain episesamin at high concentration.

FIG. 1 shows an outline of the invention apparatus generally indicated by 1 for producing the episesamin-containing composition, and FIG. 2 shows its external appearance. The apparatus 1 for producing the episesamin-containing composition comprises an isomerizing unit 2 and a crystallizing unit 3 that performs recrystallization. The isomerizing unit 2 has a mixing vessel 21 in which a sesamin containing oil or fat that has a sesamin-containing composition dissolved in an oil or fat is mixed with an acidic catalyst. The mixing vessel 21 is a reaction vessel in which sesamin is brought into contact with an acidic catalyst to effect an isomerization reaction; in order to ensure that the isomerization reaction will proceed, the mixing vessel 21 is preferably equipped with a heating means (not shown), which is desirably capable of heating at 60-160° C., preferably at 80-140° C., and holding that temperature for a period of 5-60 minutes, preferably 10-30 minutes. Ordinary heating means may be employed, such as an electric heater and a means of using heated steam. In addition, an agitating means 22 is desirably provided in generally the center of the mixing vessel in order to make the temperature of the reaction solution in the mixing vessel uniform and/or promote the reaction by increasing the frequency of contact between the sesamin-containing oil or fat and the acidic catalyst. The agitating means 22 comprises an agitator 221 composed of an agitating shaft 221*a* and agitating blades 221*b*, with a drive unit 222 provided above the agitator 221.

The sesamin oil may be an oil or fat that contains a sufficient enough amount of sesamin to be crystallized with the crystallizing unit and it may be exemplified by sesame oil obtained by supercritical extraction; however, in order to assure efficient precipitation of episesamin, it is preferred to use an oil or fat that is mixed with sesamin or the sesamin-containing composition which is then dissolved in the oil or fat under heating. This step of dissolving with heat can be performed by means of the mixing vessel 21 as sesamin is being mixed with the acidic catalyst. In this case, the mixing vessel 21 is preferably equipped with an inlet through which a powder is fed and a hopper (not shown) from which it is fed.

In the isomerizing unit 2, the reaction solution containing the epimerized episesamin is taken out of the mixing vessel 21 through an outlet 23 and fed into the crystallizing unit 3 via fluid channels (51, 52) between which a filtering means 4 is provided. To open and close the outlet 23, an ON/OFF valve (not shown) is provided, which remains closed while epimerization reaction takes place within the mixing vessel 21 and is opened after the reaction ends, allowing the reaction solution to be forwarded. The reaction solution discharged from the mixing vessel 21 passes through the fluid channel (reaction solution feed pipe 51) to be fed to the filtering means 4. The filtering means may be of any type that can remove the acidic catalyst, as specifically exemplified by a membrane filter, but it is necessary to choose one that is operable at the temperature (high temperature) of the reaction solution. For rapid filtration, the filtering means 4 is preferably equipped with a pressurizing means or a suction means. In addition, if the temperature of the reaction solution drops, the crystal of sesamin or episesamin may potentially precipitate, so it is preferred to equip the filtering means 4 with a heating means. Included among the heating means is a high temperature holding means which suppresses the temperature of the reaction solution from dropping. An example of the high temperature holding means may be an insulator that covers the reaction solution feed pipe 51 and the filtering means 4.

The filtrate separated by the filtering means 4 passes through the filtrate feed pipe 52 to be fed into a crystallizing vessel 31 in the crystallizing unit 3. The apparatus of the present invention for producing the episesamin-containing composition depends on the difference in solubility between sesamin and episesamin and on the process of recrystallization in the oil or fat for separating episesamin from the mixture of sesamin and episesamin which are similar in structure. To be more specific, the episesamin-containing reaction solution in a hot state is cooled in the crystallizing vessel 31 to a temperature that provides a lower solubility than saturated solubility, whereupon the supersaturated episesamin is precipitated. Therefore, the crystallizing vessel 31 is preferably equipped with a cooling means (not shown). The cooling means may work through cooling by heat exchange with a coolant or it may work through cooling by vaporizing part of the solvent under reduced pressure; however, if the cooling rate is too fast, the density of the precipitating crystal becomes so coarse that it may potentially involve a large amount of the solvent oil or fat; hence, in the case of cooling with a coolant, it is recommended not to use ice and the like as the coolant but use water or air at about zero to about ordinary temperatures, preferably at about 5 to about 20° C. The crystallizing vessel 31 is preferably equipped with an agitating means 32 in generally its center for the purpose of making the temperature of the filtrate in the vessel uniform. The agitating means 32 comprises an agitator 321 composed of an agitating shaft 321*a* and agitating blades 321*b*, with a drive unit 322 provided above the agitator 321. At the point in time when the filtrate in the crystallizing vessel 31 has been cooled down to a certain extent, seed crystals are preferably fed in for the purpose of realizing consistent crystallization; to this end, the crystallizing vessel 31 is preferably fitted with an inlet through which seed crystals are fed in.

If the mixing vessel 21 and the crystallizing vessel 31 are fitted with an inspection window, one can confirm that sesamin and episesamin have been dissolved under heating, that clay treatment has been performed, and that recrystallization (crystal precipitation by crystallization) has occurred.

The slurry containing the precipitated crystal is recovered from the crystallizing vessel 31 through an outlet 33, thereby yielding the desired episesamin. For the purpose of isolating the crystal from the slurry, a crystal separating means such as a suction or otherwise filtering unit or a centrifugation unit may be provided on a line either continuous or discontinuous from the apparatus of the present invention for producing the enriched episesamin-containing composition. In addition, a means by which the filtrate freed of the desired crystal is fed again into the mixing vessel 21 may be employed for a second use of the solvent oil or fat. Further in addition, for the purpose of increasing the purity of episesamin, a means by which the separated episesamin crystal is washed with an added organic solvent such as ethyl alcohol, then filtered, and optionally dried may be provided on a line either continuous or discontinuous from the apparatus of the present invention for producing the episesamin-containing composition.

EXAMPLES

The present invention will now be described more specifically by reference to the following examples, which are by no means intended to limit the present invention.

Test Examples

Epimerization of Sesamin

Test Example 1

Twenty grams of toluene was weighed as a solvent in a 3-necked flask of 100 ml in capacity; the flask was then charged with 4.0 g of a sesamin-episesamin mixture (in a sesamin/episesamin compositional ratio of 99.1/0.9) and heated in an oil bath at 110° C. under agitation until the mixture was completely dissolved. To the solution, 0.6 g of activated clay (product of MIZUSAWA INDUSTRIAL CHEMICALS, LTD., with the trade name "GALLEON EARTH V2R") was added as an acidic catalyst and the mixture was stirred at 110° C. Subsequently, the reaction was traced over time by HPLC analysis under the following conditions; 5 minutes later, episesamin was found to have been produced in a yield of about 48%.
(HPLC Conditions)
Column: Inertsil ODS-3 (product of GL-SCIENCE) 4.6×150 mm;
Column temperature: 25° C.
Mobile phase: methyl alcohol/water=7:3
Flow rate: 1 ml/min
Detector: UV 290 nm Test Example 2

Twenty grams of benzene was weighed as a solvent in a 3-necked flask of 100 ml in capacity; the flask was then charged with 4.0 g of a sesamin-episesamin mixture (in a sesamin/episesamin compositional ratio of 99.1/0.9) and heated in an oil bath at 80° C. under agitation until the mixture was completely dissolved. To the solution, 0.6 g of activated clay (product of MIZUSAWA INDUSTRIAL CHEMICALS, LTD., with the trade name "GALLEON EARTH V2R") was added as an acidic catalyst and the mixture was stirred at 110° C. Subsequently, the reaction was traced over time by HPLC analysis under the same conditions as in Test Example 1; one hour later, episesamin was found to have been produced in a yield of about 49%.

Test Example 3

Twenty grams of toluene was weighed as a solvent in a 3-necked flask of 100 ml in capacity; the flask was then charged with 4.0 g of a sesamin-episesamin mixture (in a sesamin/episesamin compositional ratio of 99.1/0.9) and heated in an oil bath at 110° C. under agitation until the mixture was completely dissolved. To the solution, 0.78 g of D-camphor-10-sulfonic acid (product of nacalai tesque) was added as an acidic catalyst and the mixture was stirred at 110° C. Subsequently, the reaction was traced over time by HPLC analysis under the same conditions as in Test Example 1; the production of episesamin increased gradually and 20 hours later, episesamin was found to have been produced in a yield of about 48%. When the addition of D-camphor-10-sulfonic acid was increased to 1.30 g, episesamin was produced in a yield of about 43% after the passage of 2 hours; 18 hours later following the reaction overnight, the yield increased to about 49%, giving an episesamin/sesamin production ratio of nearly 1:1.

Test Example 4

Ethanol (5.0 ml) was weighed as a solvent in a test tube with a removable cap that had a capacity of 70 mL; the test tube was then charged with 96 mg of a sesamin-episesamin mixture (in a sesamin/episesamin compositional ratio of 99.1/0.9), fitted with the cap and heated in an oil bath at 83° C. under agitation until the mixture was completely dissolved. To the solution, 1.2 ml of hydrochloric acid (product of nacalai tesque, containing 35% HCl) was added as an acidic catalyst and after replacing the cap, the mixture was stirred at 110° C. Subsequently, the reaction was traced over time by HPLC analysis under the same conditions as in Test Example 1; 2 hours later, episesamin was found to have been produced in a yield of about 49%.

Test Example 5

An eggplant type flask of 20 ml in capacity was charged with 5.0 ml of ethylene chloride and 96 mg of a sesamin-episesamin mixture (in a sesamin/episesamin compositional ratio of 99.1/0.9); thereafter, at a reduced temperature of −83° C., the mixture was agitated for 10 minutes under nitrogen bubbling. To the solution, 72 mg of aluminum chloride (product of Sigma Aldrich) was added as an acidic catalyst. Subsequently, the reaction was traced over time by HPLC analysis under the same conditions as in Test Example 1; 30 minutes later, episesamin was found to have been produced in a yield of about 21%.

Example 1

Twenty grams of an oil or fat was weighed in an eggplant type flask of 50 ml in capacity; the flask was then charged with 2.8 g of a sesamin-episesamin mixture (in a sesamin/episesamin compositional ratio of 99.1/0.9) and heated in an oil bath at 120° C. under agitation until the mixture was completely dissolved. To the solution, 0.4 g of activated clay (product of MIZUSAWA INDUSTRIAL CHEMICALS, LTD., with the trade name "GALLEON EARTH V2R") was added as an acidic catalyst; following a 30-min treatment at 120° C., the waste clay was removed by filtration. A portion of the filtrate was taken as a sample for HPLC analysis (sample 1).

The remaining liquid was slowly cooled by standing in a 20° C. environment; when the liquid temperature reached 60° C., 2.8 mg of 100% episesamin seed crystals were added and crystallization was performed for 30 minutes in a 20° C. environment. The liquid containing precipitating crystals was subjected to solid-liquid separation by suction filtration and the remaining solvent in the crystal mixture was washed off with 99.5% ethyl alcohol. The thus recovered crystal mixture (sample 2) was subjected to HPLC under the following conditions for analyzing the composition of sesamin/episesamin. The results of analysis are shown in Table 1 (in which the episesamin purity means the concentration (wt %) of episesamin in the crystal mixture).

(HPLC Conditions)
Column: Inertsil ODS-3 (product of GL-SCIENCE) 4.6×150 mm;
Column temperature: 40° C.
Mobile phase: methyl alcohol/water=7:3
Flow rate: 1 ml/min
Detector: UV 290 nm Viscosity measurement was conducted with a viscotester Model VT-04 (product of RION Co., Ltd.) rotor No. 3 and the oil or fat was adjusted to a liquid temperature of 20° C. The rotating speed was 62.5 rpm and the reading obtained 10 seconds after starting the rotor was substituted for the viscosity of the oil or fat tested.

TABLE 1

| Oil or fat | Oil or fat's viscosity (dPa · s) | Composition of sesamin/episesamin in (sample 1) reaction filtrate (%) | Episesamin purity in (sample 2) episesamin-rich composition (%) |
| --- | --- | --- | --- |
| MCT | 0.30 or less | 44.9/46.6 | 95.1 |
| Diacyl glycerol | 0.53 | 53.7/40.2 | 83.8 |
| Olive oil | 0.60 | 45.1/47.0 | 86.3 |
| Sesame salad oil | 0.45 | 62.3/32.3 | 67.2 |
| Soybean oil | 0.39 | 49.5/43.7 | 88.4 |
| Wheat germ oil | 0.50 | 55.7/39.0 | 37.0 |
| Rice germ oil | 0.61 | 50.4/43.4 | 80.5 |
| Rapeseed oil | 0.47 | 50.1/43.1 | 74.5 |
| Corn oil | 0.40 | 48.0/45.0 | 76.0 |
| Sunflower seed oil | 0.62 | 47.9/45.1 | 81.2 |
| Roasted sesame oil | 0.50 | 80.5/15.3 | 10.3 |
| Octaonic acid | 0.30 or less | 48.3/44.2 | 94.8 |
| Octyl acetate | 0.30 or less | 45.2/47.2 | 97.2 |

As is clear from Table 1, compositions with 65 wt % and more episesamin could be produced when MCT, diacyl glycerol, olive oil, sesame salad oil, soybean oil, rice germ oil, rapeseed oil, corn oil, sunflower seed oil, octaonic acid and octyl acetate were used as oil or fat. In particular, it was found that compositions with 80 wt % and more episesamin could be produced when diacyl glycerol, olive oil, soybean oil, rice germ oil, rapeseed oil and sunflower seed oil were used, and that compositions with 90 wt % and more episesamin could be produced when MCT, octaonic acid and octyl acetate were used.

Example 2

Twenty grams of an oil or fat was weighed in an eggplant type flask of 50 ml in capacity; the flask was then charged with 4.0 g of a sesamin-episesamin mixture (in a sesamin/episesamin compositional ratio of 55/45) and heated in an oil bath at 120° C. under agitation until the mixture was completely dissolved. To the solution, 0.57 g of activated clay (product of MIZUSAWA INDUSTRIAL CHEMICALS, LTD., with the trade name "GALLEON EARTH V2R") was added as an acidic catalyst; following a 30-min treatment at 120° C., the waste clay was removed by filtration. A portion of the filtrate was taken as a sample for HPLC analysis (sample 1). The remaining liquid was slowly cooled by standing in a 20° C. environment; when the liquid temperature reached 60° C., 4.0 mg of 100% episesamin seed crystals were added and crystallization was performed for 30 minutes in a 20° C. environment. The liquid containing precipitating crystals was subjected to solid-liquid separation by suction filtration and the remaining solvent in the crystal mixture was washed off with 99.5% ethyl alcohol. The thus recovered crystal mixture was designated (sample 2).

Similarly, 20 g of an oil or fat (MCT; ACTOR M-1 manufactured by RIKEN VITAMIN CO., LTD.) was weighed in an eggplant type flask of 50 ml in capacity; the flask was then charged with 4.0 g of a sesamin-episesamin mixture (in a sesamin/episesamin compositional ratio of 55/45) and heated in an oil bath at 120° C. under agitation until the mixture was completely dissolved; a portion of the solution was taken as a sample for HPLC analysis (sample 3). The remaining liquid was slowly cooled by standing in a 20° C. environment; when the liquid temperature reached 60° C., 4.0 mg of 100% episesamin seed crystals were added and crystallization was performed for 30 minutes in a 20° C. environment. The liquid containing precipitating crystals was subjected to solid-liquid separation by suction filtration and the remaining solvent in the crystal mixture was washed off with 99.5% ethyl alcohol. The thus recovered crystal mixture (sample 4) was subjected to HPLC for analyzing the composition of sesamin/episesamin. The HPLC conditions were the same as in Example 1. The results are shown in Table 2.

TABLE 2

| Clay treatment | Composition of sesamin/episesamin in (samples 1, 3) reaction filtrate (%) | Episesamin purity in (samples 2, 4) episesamin-rich composition (%) |
| --- | --- | --- |
| Performed | 45.9/46.3 | 94.0 |
| Not performed | 55.1/43.4 | 67.4 |

As is clear from Table 2, the clay treatment helped increase the content of episesamin in the finally obtained composition.

Example 3

Twenty grams of an oil or fat (MCT; ACTOR M-1 manufactured by RIKEN VITAMIN CO., LTD.) was weighed in an eggplant type flask of 50 ml in capacity; the flask was then charged with 2.8 g of a sesamin-episesamin mixture (in a sesamin/episesamin compositional ratio of 99.1/0.9) and heated in an oil bath at 120° C. under agitation until the mixture was completely dissolved. To the solution, 0.4 g of acid clay or activated clay (each being manufactured by MIZUSAWA INDUSTRIAL CHEMICALS, LTD.) was added as an acidic catalyst; following a 30-min treatment at 120° C., the waste clay was removed by filtration. A portion of the filtrate was taken as a sample for HPLC analysis. The thus prepared sample was subjected to HPLC under the following conditions for analyzing the composition of sesamin/episesamin. The results of analysis are shown in Table 3.

(HPLC Conditions)
Column: Inertsil ODS-3 (product of GL-SCIENCE) 4.6×150 mm;
Column temperature: 40° C.
Mobile phase: methyl alcohol/water=7:3
Flow rate: 1 ml/min
Detector: UV 290 nm

TABLE 3

| Trade name | Common name | Particle size (mm) | pH (5% suspension) | Composition of sesamin/episesamin in reaction filtrate (%) |
|---|---|---|---|---|
| MIZUKA-ACE #200 | acid clay | fine powder | 6.4 | 91.8/6.5 |
| MIZUKA-ACE #300 | acid clay | fine powder | 8.5 | 97.0/1.1 |
| MIZUKA-ACE #400 | acid clay | fine powder | 5.6 | 84.6/13.3 |
| GALLEONITE #036 | acid clay | 0.71-0.25 | 8.2 | 96.3/1.6 |
| GALLEONITE #0612 | acid clay | 3.4-1.4 | 7.5 | 96.3/1.5 |
| GALLEONITE #251 | activated clay | 4.0-1.7 | 2.9 | 69.3/26.1 |
| GALLEONITE #136 | activated clay | 0.71-0.25 | 2.9 | 88.9/8.3 |
| GALLEON EARTH V2 | activated clay | fine powder | 2.9 | 45.3/46.7 |
| GALLEON EARTH V2R | activated clay | fine powder | 2.9 | 44.9/46.6 |

* fine powder: 80-95% pass at 90 μm

Example 4

As shown in Example 3, the acid clay did not cause comparable isomerization reaction, so a strong acid was added to the reaction solution and check was made to see whether it would give a result comparable to that obtained with the activated clay (the pH of the suspension as measured with a strip of pH test paper was about 1.)

Sixteen milliliters of MCT (ACTOR M-1 manufactured by RIKEN VITAMIN CO., LTD.) and 4 ml of 5N HCl were weighed in an eggplant type flask of 50 ml in capacity; the flask was then charged with 2.8 g of a sesamin-episesamin mixture (in a sesamin/episesamin compositional ratio of 99.1/0.9) and, after being fitted with a reflux pipe, the flask was heated in an oil bath at 120° C. under agitation until the mixture was completely dissolved. To the solution, 0.4 g of acid clay (MIZUKA-ACE #400 manufactured by MIZUSAWA INDUSTRIAL CHEMICALS, LTD.) was added and reaction was carried out at 120° C. for 30 minutes. After the end of the reaction, the waste clay was removed by filtration and a portion of the filtrate was taken as a sample for HPLC analysis. The conditions of analysis were the same as in Example 1. As a result of the HPLC analysis, the sesamin/episesamin proportion was 53.7/41.0, revealing that the isomerization reaction was comparable to that obtained with the activated clay.

Example 5

Episesamin was produced from a sesamin-containing oil or fat using an apparatus for producing enriched episesamin-containing compositions that is indicated by 1 in FIG. 1. Specifically, 2500 g of MCT (ACTOR M-1 manufactured by RIKEN VITAMIN CO., LTD.) was weighed in the mixing vessel 21, which was then charged with 360 g of a sesamin-episesamin mixture (in a sesamin/episesamin compositional ratio of 99.1/0.9) and heated in an oil bath at 120° C. under agitation until the mixture was sufficiently dissolved to form a sesamin-containing oil or fat solution. Into the mixing vessel 21 now containing the oil or fat solution, 54 g of an acidic catalyst (activated clay manufactured by MIZUSAWA INDUSTRIAL CHEMICALS, LTD. and having the trade name "GALLEON EARTH V2R") was added; following a 30-min treatment at 120° C., the treated liquid was flowed under pressure through a membrane filter (filtering means 4) to cause simultaneous removal of the waste clay. The resulting liquid (ca. 100° C.) was received by the crystallizing vessel 31 in the crystallizing unit 3 and slowly cooled with cold water. About 15 minutes later when the liquid temperature reached 60° C., 720 mg of episesamin (99.9% pure) was charged as seed crystals and crystallization was performed for 90 minutes under mild agitation. The resulting slurry (ca. 25-30° C.) was recovered through the outlet 33.

Thereafter, solid-liquid separation was performed by suction filtration and the crystal was washed with ethanol to give the desired crystal in an amount of 90.8 g (yield, 26.0%). The thus obtained sample was subjected to HPLC under the following conditions for analyzing the composition of sesamin/episesamin; the episesamin purity was 95.6%.

(HPLC Conditions)
Column: Inertsil ODS-3 (product of GL-SCIENCE) 4.6×150 mm;
Column temperature: 40° C.
Mobile phase: methyl alcohol/water=7:3
Flow rate: 1 ml/min
Detector: UV 290 nm

INDUSTRIAL APPLICABILITY

According to the present invention, 100% pure sesamin or a sesamin-containing composition, for example, a mixture that contains both sesamin and episesamin is used as a starting feed and, as a result, compositions that contain episesamin in a concentration greater than 50 wt % can be produced conveniently and at high yield.

The invention claimed is:

1. A process for producing an episesamin-rich composition having episesamin at a concentration greater than 50 wt % on the basis of the sum weight of sesamin and episesamin contained in the composition, comprising the steps of:
    applying epimerization to sesamin or a sesamin-containing composition so that at least part of the sesamin is converted to episesamin; and
    selectively crystallizing episesamin by recrystallization in an oil or fat to produce a composition having episesamin at a concentration greater than 50 wt % on the basis of the sum weight of sesamin and episesamin contained in the composition.

2. The process according to claim 1, wherein the episesamin-rich composition is precipitated crystal and contains episesamin at a concentration 60 wt % and upward on the basis of the sum weight of sesamin and episesamin contained in the composition.

3. The process according to claim 1, wherein the episesamin-rich composition contains episesamin at a concentration 70 wt % and upward on the basis of the sum weight of sesamin and episesamin contained in the composition.

4. The process according to claim 1, which further includes the step of dissolving the sesamin or sesamin-containing composition in an oil or fat under heating either prior to or after epimerization, thereby preparing a solution.

5. The process according to claim 4, wherein the oil or fat is at least one member selected from among MCT (middle-chain fatty acid triglyceride), diacyl glycerol, sesame salad oil, olive oil, soybean oil, rapeseed oil, corn oil, rice germ oil, and sunflower seed oil.

6. The process according to claim 4, wherein the oil or fat is MCT (middle-chain fatty acid triglyceride).

7. The process according to claim 1, wherein the epimerization is an acidic catalyst treatment.

8. The process according to claim 7, wherein the acidic catalyst treatment consists of making contact with activated clay or acid clay.

9. The process according to claim 8, wherein the activated clay or acid clay is one that has been adjusted to have a pH of 3.7 or less in the form of a 5% aqueous suspension.

10. The process according to claim 8, wherein the activated clay or acid clay has a specific surface area of 150-350 $m^2/g$.

11. The process according to claim 4, which further includes the step of recovering by filtration the crystal that has precipitated by recrystallization.

12. The process according to claim 11, wherein the filtrate formed in the step of recovery by filtration is recycled to the step of preparing the solution.

13. The process according to claim 1, wherein the starting feed is either nearly 100% sesamin or a mixture of sesamin and episesamin at a sesamin to episesamin weight ratio between 99.9:0.1 and 40:60.

* * * * *